United States Patent [19]
Ogiu

[11] Patent Number: 4,746,975
[45] Date of Patent: May 24, 1988

[54] ELECTRONIC ENDSCOPE APPARATUS

[75] Inventor: Hisao Ogiu, Tokyo, Japan

[73] Assignee: Olympus Optical Co., Ltd., Japan

[21] Appl. No.: 937,749

[22] Filed: Dec. 4, 1986

[30] Foreign Application Priority Data

Dec. 6, 1985 [JP] Japan .................. 60-274750

[51] Int. Cl.⁴ .............................................. H04N 7/18
[52] U.S. Cl. .................. 358/98; 358/213.26; 128/4
[58] Field of Search ............... 358/98, 213.11, 213.26; 128/4, 6

[56] References Cited

U.S. PATENT DOCUMENTS

| | | | |
|---|---|---|---|
| 4,261,344 | 4/1981 | Moore et al. | 358/98 |
| 4,426,664 | 1/1984 | Nagumo et al. | 358/213.26 |
| 4,517,976 | 5/1985 | Murakoshi et al. | 128/4 |
| 4,539,586 | 9/1985 | Danna | 358/98 |
| 4,604,992 | 8/1986 | Sato | 358/98 |
| 4,663,657 | 5/1987 | Nagasaki et al. | 358/98 |
| 4,667,230 | 5/1987 | Arakawa et al. | 358/98 |

FOREIGN PATENT DOCUMENTS 2515148 10/1976 Fed. Rep. of Germany.
3429811 4/1985 Fed. Rep. of Germany.

Primary Examiner—James J. Groody
Assistant Examiner—John K. Peng

[57] ABSTRACT

An electronic endoscope apparatus having an endoscope with a distal portion containing a solid-state image sensor. The endoscope has a connector section. A frequency divider is provided within this connector section. A video processor is coupled to the endoscope. The video processor outputs a constant-frequency signal, which is supplied to the frequency divider. The frequency divider divides this signal with a frequency division rate corresponding to the number of pixels which the image sensor has.

11 Claims, 2 Drawing Sheets

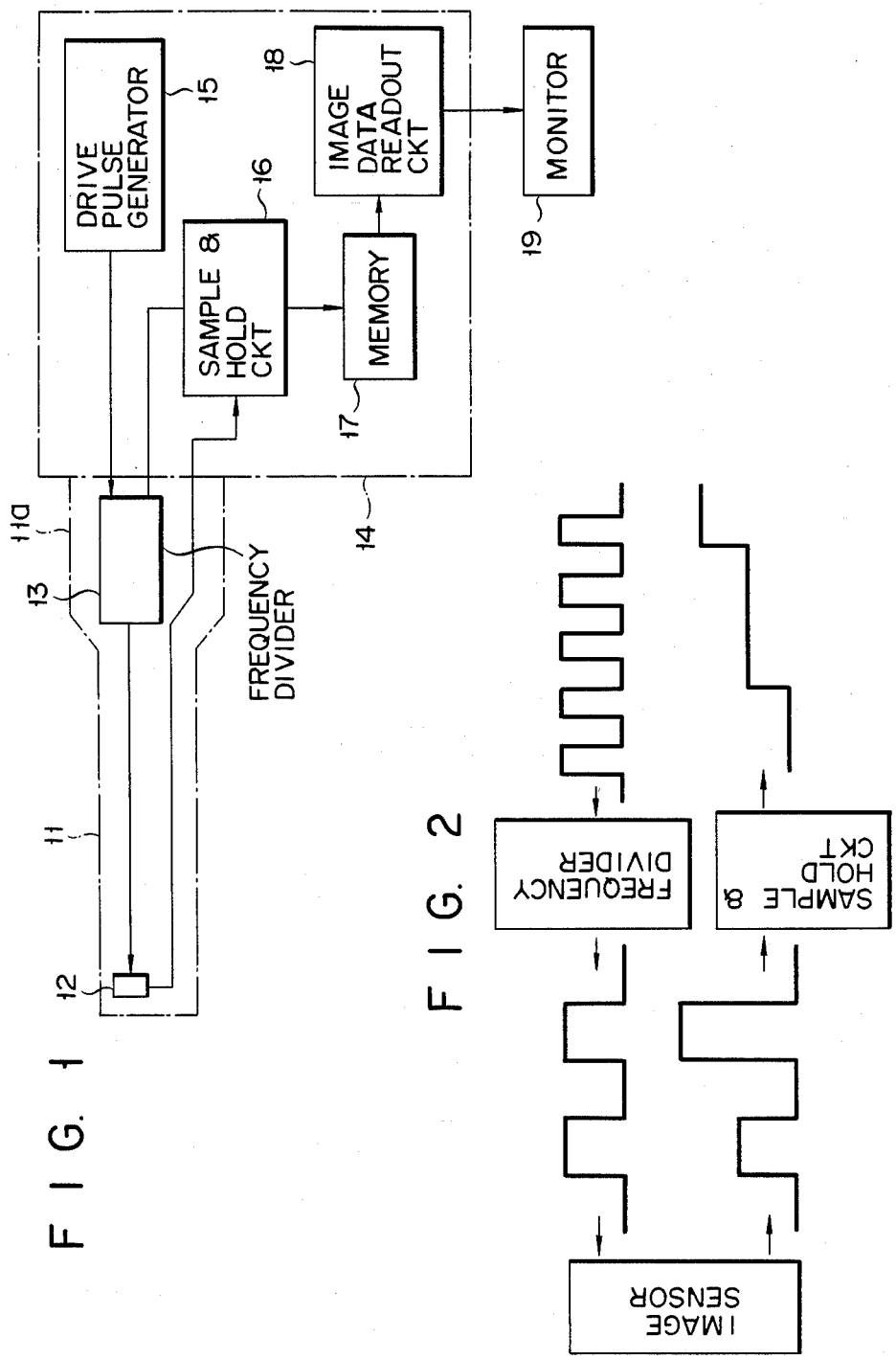

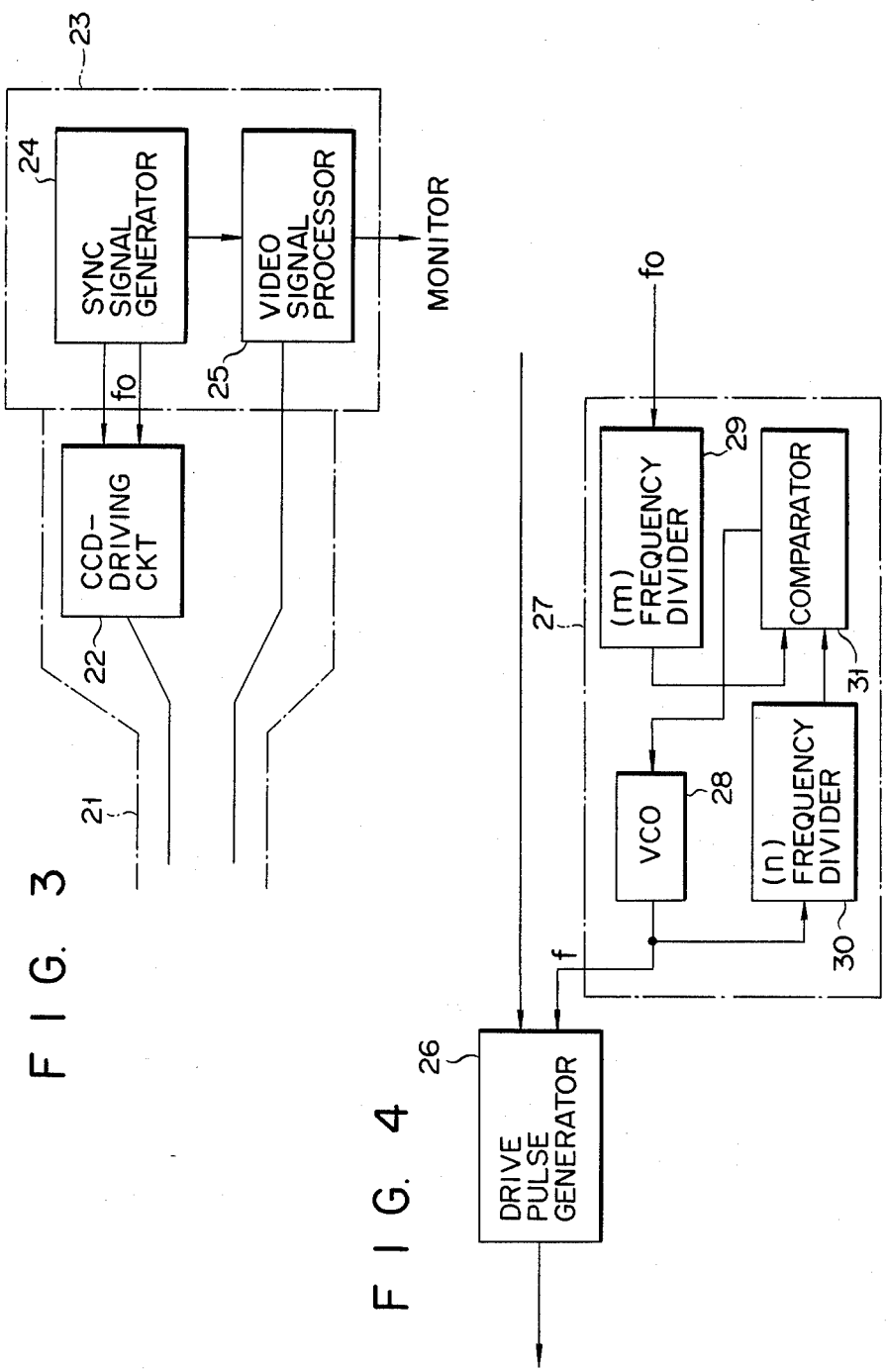

ELECTRONIC ENDOSCOPE APPARATUS

BACKGROUND OF THE INVENTION

The present invention relates to an endoscope and, more particularly to an electronic endoscope apparatus having a solid-state image sensor at its distal end.

In the conventional electronic type endoscopes that have a solid-state image sensor at the distal end, the image signals output by the sensor are supplied to a video processor through a cable connecting the sensor to the video processor. The video processor processes these signals. The processed signals are input to a monitor, which displays the endoscopic image of the region interest which has been scanned by the solid-state sensor. The number of pixels required in a specific type of an endoscope is different from the number required in another type of an endoscope. Hence, when various types of endoscopes are used, various types of video processors must be used in combination with the respective endoscopes. Such system, therefore, requires a plurality of video processors, so that it is not only expensive, but also is difficult to operate. For the same reason, the system occupies a great space.

SUMMARY OF THE INVENTION

It is an object of this invention to provide an electronic endoscope apparatus which can provide an endoscopic image, regardless of the number of pixels of the solid-state image sensor employed in the apparatus.

According to the present invention, there is provided an electronic endoscope apparatus comprising a solid-state image sensor arranged in a distal end, and a drive converter for changing the frequency of pulses for driving the image sensor, in accordance with the number of pixels of the image sensor.

BRIEF DESCRIPTION OF THE DRAWINGS

FIG. 1 is a block circuit diagram showing an electronic endoscope apparatus according to one embodiment of the present invention;

FIG. 2 shows the waveform of pulse signals, explaining the circuit shown in FIG. 1;

FIG. 3 is a block diagram showing an electronic endoscope apparatus according to another embodiment of the invention; and FIG. 4 is a circuit diagram of the CCD-driving circuit used in the apparatus shown in FIG. 3.

DETAILED DESCRIPTION OF THE PREFERRED EMBODIMENTS

As is shown in FIG. 1, an electronic endoscope apparatus of this invention comprises an electronic endoscope 11. Solid-state image sensor 12 is provided in the distal end of endoscope 11. Frequency divider 13 is arranged in connector section 11a of endoscope 11. This frequency divider is used as a means for adjusting the frequency of pulses for driving image sensor 12. The output of frequency divider 13 is coupled to image sensor 12. Electronic endoscope 11 is connected by a connector to video processor 14.

Video processor 14 comprises drive pulse generator 15 and sample-and-hold circuit 16. Drive pulse generator 15 generates the signals having a frequency which is an integral multiple of the frequency of the drive pulse signals, which is required to drive the solid-state image sensor 12 having as many pixels as is practically possible. The horizontal frequency of the drive pulse signals is defined by a multiple of the number of the entire pixels and a frame frequency, while the vertical frequency thereof is defined by a multiple of the number of the vertical pixels and the frame frequency.

When the maximum number of the pixels is 140,000 and the frame frequency is 30 Hz, the drive pulse frequency is 4.2 MHz. If the number of the pixels of a conventional image sensor is 100,000 and the frame frequency is 30 Hz, the drive pulse frequency is 3 MHz. The drive pulse frequency in a frame sequence system is three times as that in the conventional mosaic filter system.

The output of pulse generator 15 is coupled to frequency divider 13 which frequency-divides the output signal of the pulse generator 15 at the frequency suitable for driving the image sensor 12. Sample-and-hold circuit 16 is connected to the image signal-outputting section of image sensor 12, thereby to sample video signals in synchronism with the output signal of frequency divider 13. Circuit 16 is also connected to memory 17, which in turn is coupled to image data readout circuit 18. Monitor 19 is connected to circuit 18.

A light-guiding fiber bundle (not shown) is provided within endoscope 11. The fiber bundle is used to guide illumination light into a body cavity from a light source (not shown) which is provided in video processor 14.

When the power supply switch of video processor 14 is turned on, the light source is turned on. Simultaneously, drive pulse generator 15 starts generating drive pulses. The drive pulses, which have a relatively high frequency as shown in FIG. 2, are supplied to frequency divider 13. Frequency divider 13 has a frequency division rate which can be changed in accordance with the number of the pixels used in solid-state image sensor 12. Hence, when drive pulse generator 15 supplies drive pulses to frequency divider 13, frequency divider 13 can divide the frequency of these pulses (primary drive pulses), thereby outputting secondary drive pulses having such a frequency as is suitable for driving solid-state image sensor 12. The secondary drive pulses are supplied to image sensor 12. Image sensor 12 is driven by the secondary drive pulses, and outputs image signals representing the image of a region of interest within the body cavity. These image signals, or primary video signals, are sampled and held by sample-and-hold circuit 16 in synchronism with the secondary drive pulses supplied from frequency divider 13 to sample-and-hold circuit 16, and are converted to secondary video signals. The secondary video signals, which are digital signals, are converted to analog signals. The analog signals are input to monitor 19. Monitor 19 displays the endoscopic image of the region of interest which has been scanned by image sensor 12.

As is stated above, since the frequency division rate of frequency divider 13 can be changed to the value corresponding to the number of the pixels used in solid-state image sensor 12, video processor 14 can be used in combination with any solid-state image sensor, no matter how many pixels the image sensor has. In other words, video processor 14 is compatible with any electronic endoscope having a solid-state image sensor.

In the embodiment of FIG. 1, the frequency division rate of frequency divider 13 is given by dividing one with an integer. Therefore, the number of pixels, which the image sensor can have, is determined by this integer. Hence, the number of pixels is limited. The number of pixels is less limitative in another embodiment of the invention, illustrated in FIG. 3. This embodiment has CCD-driving circuit 22 provided within the connector section of an endoscope 21. Endoscope 21 is coupled to video processor 23 including sync signal generator 24 and video signal processor 25.

As is shown in FIG. 4, CCD-driving circuit 22 comprises drive pulse generator 26 and PLL circuit 27. As is well known, PLL circuit 27 comprises VCO (voltage-controlled oscillator) 28, m-frequency divider 29, n-frequency divider 30, and comparator 31. Reference clock signal $f_0$ is supplied from sync signal generator 24 to m-frequency divider 29. Divider 29 divides the frequency of clock signal $f_0$, and VCO 28 outputs a signal f. The relation between signals $f_0$ and f is given by:

$$f = (n/m) f_0$$

where the value of n/m is determined by the number of pixels of the CCD (charge-coupled image sensor) used in this embodiment.

When video processor 23 is turned on, sync signal generator 24 generates a vertical sync signal, a horizontal sync signal and reference clock signal $f_0$. Both sync signals are supplied to drive pulse generator 26, and signal $f_0$ is supplied to PLL circuit 27, as is illustrated in FIG. 4. Reference clock signal $f_0$ is processed by circuit 27 in accordance with the value of n/m which corresponds to the number of pixels which the CCD has. As a result, PLL circuit 27 outputs signal f. Signal f is input to drive pulse generator 26. Drive pulse generator 26 receives the sync signals and signal f, and outputs a CCD-driving pulses. The CCD-driving pulses drive the CCD, which therefore outputs video signals. The video signals are input to video signal processor 25. Video signal processor 25 supplies the analog video signals to monitor 19, with sync signals supplied from sync signal generator 24. Monitor 19 displays the endoscopic image represented by the video signals.

In the embodiment of FIGS. 3 and 4, division frequency rate "m" of frequency divider 29, and frequency division rate "n" of frequency divider 30 can be selected such that the value of n/m corresponds to the number of pixels of any CCD used in the embodiment.

Drive pulse generator 26, for directly driving image sensor 12, can be provided in connector 26, while PLL circuit 27 may be provided in video processor 23.

According to the present invention, the same video processor can be used in combination with various types of electronic endoscopes, no matter how many pixels the image sensors, which are used in the respective endoscopes, do have. Hence, the present invention helps to provide an endoscope system in which only one video processor suffices, unlike in the conventional endoscope system, and which is therefore less expensive than the conventional system. Moreover, with the endoscope system which can be provided by this invention, it is sufficient to replace only endoscopes with one another, and the system can be more easily operated than the conventional system wherein not only the endoscopes, but also the video processors must be replaced.

In the embodiments described above, the frequency divider and the CCD-driving circuit are provided in the connector sections. Nonetheless, these components can be provided anywhere in the signal supply system of the solid-state image sensor.

What is claimed is:
1. An electric endoscope apparatus comprising:
an endoscope having a distal portion containing a solid-state image sensor which has a predetermined number of pixels and is designed to be driven by drive signals, to output image signals;
a driving section including drive signal means, provided in said endoscope and connected to said image sensor for outputting the drive signals having a frequency which is determined by the number of pixels in said image sensor;
signal-processsing means provided outside said endoscope and connected to said image sensor and said drive signal means, for processing the image signals supplied from said image sensor, in synchronism with the drive signals for driving said image sensor, to output video signals; and
display means connected to said signal-processing means, for displaying an endoscopic image represented by the video signals supplied from said signal-processing means.

2. An apparatus according to claim 1, wherein said driving section comprises pulse-generating means for generating a pulse signal of a constant frequency, and wherein said drive signal means includes frequency dividing means connected to said pulse-generating means, having a frequency division rate corresponding to the number of pixels which said image sensor has, and adapted to convert said pulse signal to a drive signal having a frequency corresponding to the number of pixels which said image sensor has.

3. An apparatus according to claim 2, wherein said endoscope has a connector section containing said frequency dividing means.

4. An apparatus according to claim 1, wherein said driving section comprises signal-generating means for generating a synchronizing signal and a constant-frequency signal, and wherein said drive signal means includes a phase-locked loop circuit having a frequency division rate which can be changed in accordance with the number of pixels of said image sensor and adapted to convert the constant-frequency signal to a signal having a frequency determined by the frequency division rate, and drive signal-generating means for converting the signal, supplied from said phase-locked loop circuit, to a drive signal for driving said image sensor provided in said endoscope.

5. An apparatus according to claim 4, wherein said endoscope has a connector section containing said drive signal-generating means and said phase-locked loop circuit.

6. An apparatus according to claim 1, wherein said signal-processing means comprises sample-and-hold means to sample and hold the image signal, memory means for storing, as image data, the image signal supplied from said sample-and-hold means, and means for reading the image data from said memory means, in the form of a video signal.

7. An apparatus according to claim 1, wherein said driving section comprises signal-generating means for generating a synchronizing signal and a constant-frequency signal and a phase-locked loop circuit having a frequency division rate which can be changed in accordance with the number of pixels of said image sensor and adapted to convert the constant-frequency signal to a signal having a frequency determined by the frequency division rate, and wherein said drive signal means includes means for converting the signal, supplied from said phase-locked loop circuit, to a drive signal for driving said image sensor provided in said endoscope.

8. An apparatus according to claim 7, wherein said endoscope has a connector section containing said drive signal means.

9. An electric endoscope apparatus comprising:
an endoscope having a distal portion containing a solid-state image sensor which has a predetermined number of pixels and is designed to be driven by a drive signal, to output an image signal;
driving means for driving said image sensor, which is provided in said endoscope and connected to said image sensor for supplying the drive signal to said image sensor, said driving means generating the drive signal whose frequency corresponds to the number of pixels in said image sensor;
signal-processing means provided outside said endoscope and connected to said image sensor and said drive signal means, for processing the image signals supplied from said image sensor, in synchronism with the frequency of the drive signal, to output video signals; and
display means connected to said signal-processing means, for displaying an endoscopic image represented by the video signals supplied from said signal-processing means.

10. An electric endoscope apparatus according to claim 9, wherein said driving means includes means for pulse-generating means for generating a pulse signal of a constant frequency, and means for frequency-dividing the pulse signal received from said pulse-generating means at a frequency division rate corresponding to the number of pixels, to output the drive signal.

11. An electric endoscope apparatus according to claim 9, wherein said signal-processing means includes sample-and-hold means to sample and hold the image signal, in synchronism with the frequency of the drive signal, and means for outputting the image signal outputted from said sample-and-hold means as the video signal to said display means.

* * * * *